United States Patent [19]

Meyer et al.

[11] 4,022,195
[45] May 10, 1977

[54] COMBINED MASSAGE AND SPOT HEATING DEVICE

[75] Inventors: Roy E. Meyer, Sterling; Jerry E. Stuart, Morrison, both of Ill.

[73] Assignee: Wahl Clipper Corporation, Sterling, Ill.

[22] Filed: Apr. 14, 1976

[21] Appl. No.: 677,008

[52] U.S. Cl. .............................................. 128/24.2
[51] Int. Cl.² .................................. A61H 21/00
[58] Field of Search ............... 128/24.1, 24.2, 33, 128/41, 36

[56] References Cited

UNITED STATES PATENTS

| | | | |
|---|---|---|---|
| 3,019,785 | 2/1962 | Eiden | 128/33 |
| 3,062,203 | 11/1962 | Ziff | 128/24.1 |
| 3,220,405 | 11/1965 | Bross | 128/24.1 |
| 3,323,517 | 6/1967 | Keller | 128/24.1 |

*Primary Examiner*—Lawrence W. Trapp
*Attorney, Agent, or Firm*—Carl C. Batz

[57] ABSTRACT

A combined massage and spot heating device including a cushion adapted to be placed next to the body of a person to be treated and having a vibrating mechanism contained therein, and a switchbox containing switching means for controlling the amplitude of vibration, said means including a resistor inside the switchbox which may be cut into the vibrator circuit at certain positions of the switching means, the resistor serving to heat a heat-conducting plate associated with the switchbox to provide a facility for spot heating selected areas on the body of the person being treated.

3 Claims, 7 Drawing Figures

COMBINED MASSAGE AND SPOT HEATING DEVICE

This invention relates to a combined massaging and spot heating device. In some respects this invention is an improvement on the back massaging device set forth in the co-pending patent application Ser. No. 629,780 by John F. Wahl filed Nov. 7, 1975.

BACKGROUND

In the prior application Ser. No. 629,780, there is described in a cushion which is adapted to be placed against the back of a chair which contains a vibrator which when operated delivers a massaging effect to the back of a person sitting in a chair. The vibrator is electrically connected to an electrical source, and a simple switch is provided to turn the connection on and off.

It is found that there is a need for regulating the vibrator of such a massaging cushion so that it may be caused to vibrate at a lower amplitude and so deliver a more gentle massaging action on some occasions.

Also it is thought that it would be desirable to provide a spot heating facility which would allow the person sitting in the chair and being treated by massaging action to apply heat to his face, his neck, or to any selected part of his body.

Therefore, we have sought to satisfy both these functions and to provide apparatus which will have this double function. More particularly we have sought apparatus for accomplishing these functions in which the apparatus is contained within a switchbox separate from the cushion and in which the box itself may be moved by the person occupying the chair to apply spot heat to a selected part of his body.

DESCRIPTION

One embodiment of our invention is illustrated in the accompanying drawings in which.

Figure 1:
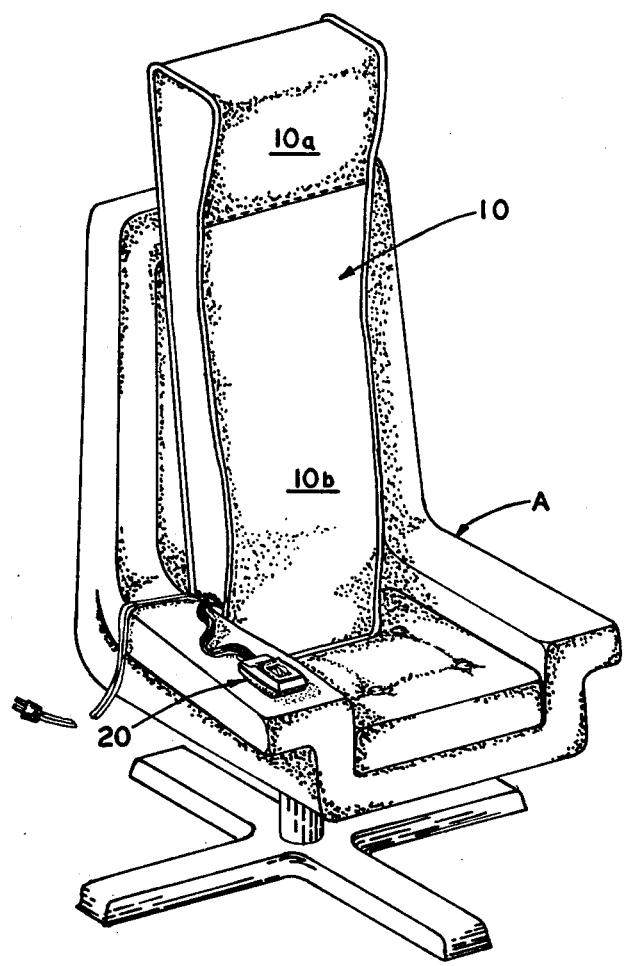
FIG. 1 is a perspective view of the improved device with the cushion in place to the back of a chair.
Figure 2:
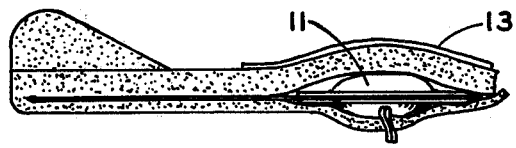
FIG. 2 is a longitudinal sectional view of the cushion showing the vibrator case in place within the cushion.
Figure 3:
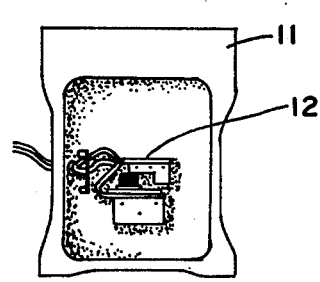
FIG. 3 is a detailed view showing the vibrator.

As illustrated, the cushion 10 is adapted to rest next to the back of chair A. The cushion has a pillow portion 10a. The thicker portion 10b of the cushion is adapted to contact the back of the person sitting in the chair and it is this portion which contains the vibrator casing 11 (see FIG. 2), and the casing 11 contains the vibrator mechanism 12. In addition to the vibrator the cushion may also contain an electrical heating pad 13. This may be located near the vibrator casing or at any desired position within the cushion.

Figure 6:
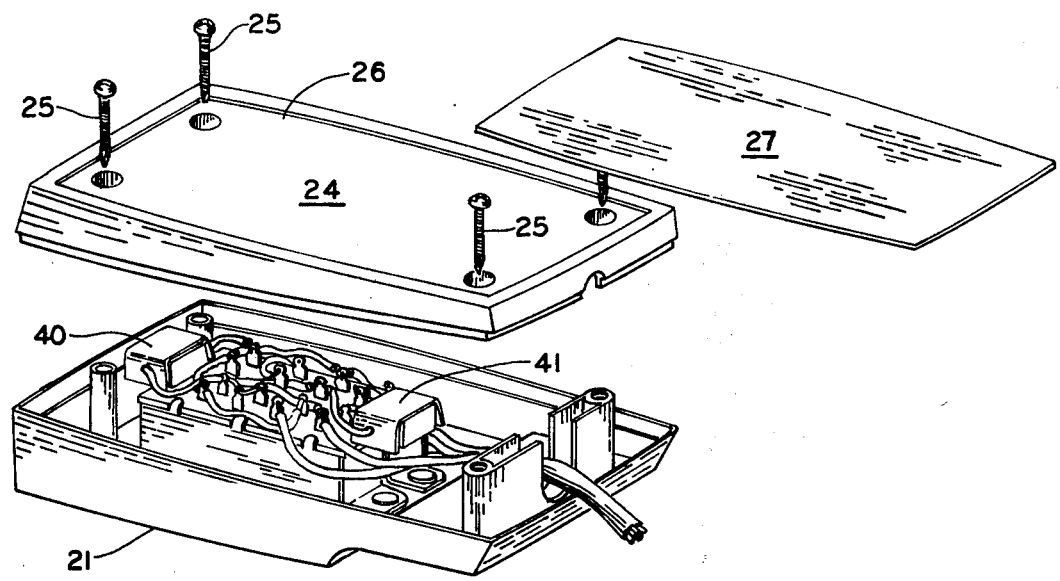
FIG. 6 is a perspective view showing the heat plate and the backside of the switchbox removed.
Figures 4, 5:
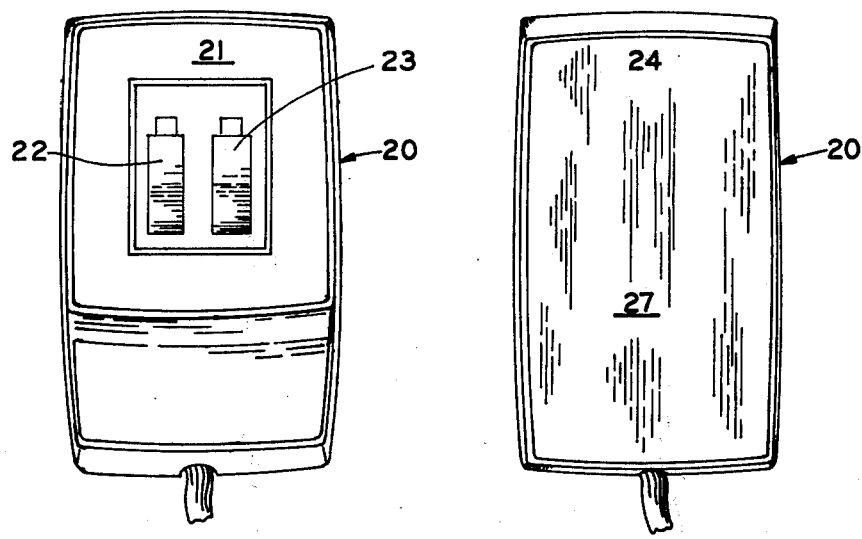
FIG. 4 is a view of the front face of the switchbox.
FIG. 5 is a view of the back face of the switchbox.

Turning now to the switchbox 20 as illustrated in FIG. 4 to 6, this box may be formed in two parts made of plastic material. The face side 21 is shown in FIG. 4 and includes the two toggles 22 and 23. The left-hand toggle 22 may be moved into one of three positions for providing high, medium or low amplitude to the vibrator. The right-hand toggle 23 may be moved to high, medium, or low positions to provide respectively high, medium or low heat to the heating pad.

In FIG. 6 the side 21 is shown inverted and the back plate 24 is attached to the part 21 by means of screws 25. On the backside of the plate 24 is an indentation 26 into which the plate 27 is fitted. Plate 27 may be made of a heat conducting metal such as brushed aluminum, and when the plate is mounted within the indentation it is held in position with its sides flush with the edges of the plastic back plate 24.

Figure 7:
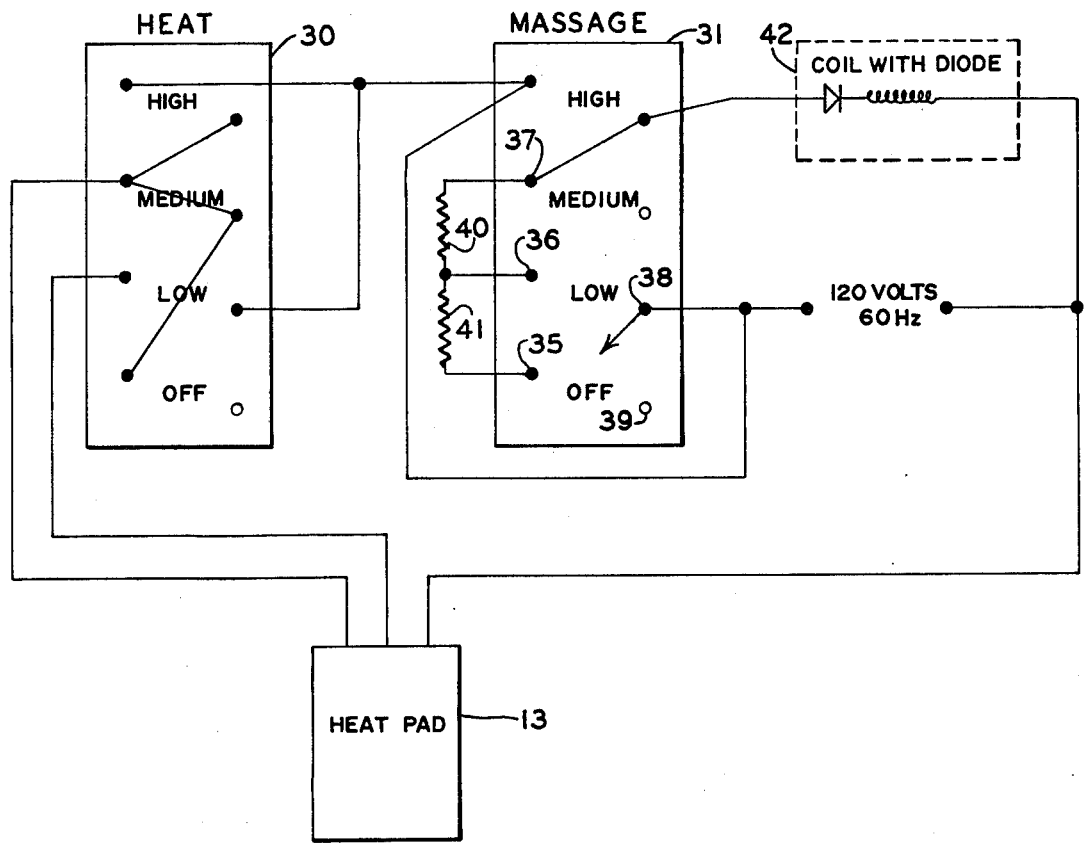
FIG. 7 is a schematic wiring diagram showing the electrical connections between the elements of the apparatus.

FIG. 7 is a schematic drawing of a wiring diagram. The toggle 23 controls the connection of the cushion heating pad in the high, medium and low positions as shown in the rectangle designation 30. The rectangle 31 to the right, contains the points 35, 36, and 37, and operation of the toggle 22 can connect the point 38 which is connected to one side of the 120 volt electrical source, to the point 39, which leaves the vibrator off, or to one of points 35, 36 or 37 depending on whether low, medium or high vibrator amplitude is desired.

A resistor 40, which is contained inside the switchbox 20, is connected between the points 36 and 37, and a second resistor 41, which is also contained within the switchbox 20, is connected between points 35 and 36. The point 37 is connected through the coil and diode 42, which represents the motor driving the vibrator, to the other side of the 120 volt source.

When the toggle 22 is moved to connect points 38 and 37, a circuit is made between the voltage source and the vibrator which causes the full 120 volts to be applied at the vibrator so as to drive the vibrator at full amplitude. Neither of resistors 40 or 41 are in the circuit. When the toggle 22 is moved to connect points 38 and 36 this cuts the resistor 40 into the vibrator circuit and cuts down the voltage to the vibrator so that it vibrates at somewhat lower amplitude. At the same time the heat coming from resistor 40 heats up the switchbox 20 and metal plate 27 becomes warm.

When the toggle 22 is moved to connect points 38 and 35 this operates to cut resistors 40 and 41 in series in the vibrator circuit which causes the vibrator to run at a still lower amplitude and at the same time to increase the amount of heat delivered by resistors so that the metal plate 27 becomes still warmer.

OPERATION

The person to receive treatment may sit in the chair A with the portion 10b of the cushion next to the small of his back. He may push the toggle 22 on switchbox 20 to its high position which produces only a strong massaging action against his back.

If the person wishes to have a more gentle massaging action or wishes to spot heat some area of his body, for example, on his face, or on his shoulder, he may move toggle 22 to medium. This produces a more gentle massage and he may then grasp the switchbox 20 and place the plate 27 next to the area on his body which he wishes to spot heat. A mild heat will be delivered to this area.

Then if the massaging action is yet a bit too strong or the heat from plate 27 not warm enough, the person being treated can move the toggle 22 to connect points 38 and 35, and this operates to produce a more mild massaging effect and a higher degree of heat at plate 27 of the switchbox.

In this way the person being treated gets a double funcion — the reduction in amplitude of vibration and also the facility of hand spot heating by having resistors 40 and 41 contained in the switchbox.

As can be more clearly seen by reference to FIG. 7 of the drawing, there is a particular advantage in Applicants' system where the electrical source is connected by the switching means associated with rectangle 31 either to off, low (both resistors connected), medium (one resistor connected) or high amplitude (with no resistors in the circuit), and where the electrical source is connected by the switching means associated with rectangle 30 either to off, low, medium or high heat to the heating pad. The switching means of rectangles 30 and 31 are both within the switchbox and it should be noted that all of the above switching functions, including the provision of spot heat at the switchbox, are accomplished with only four wires leading to or from the switchbox.

While this specific description has dealt with only one embodiment of the invention, it will be apparent to those skilled in this art that many other embodiments may be constructed and many changes may be made all within the spirit of the invention and the scope of the appended claims. We claim:

1. A combined body massaging and spot heating device comprising a cushion containing a vibrator, a switchbox separate from said cushion and containing therein a resistor, electrical means for connecting said vibrator through said box with a source of electrical energy, switch means associated with said box which at one position connects said vibrator directly to said source to produce vibration of a relatively high amplitude, and which at another position connects said vibrator to said source through said resistor to produce vibration of lower amplitude, and a heating plate on said box positioned to receive heat from said resistor.

2. A combined massaging and spot heating device as set forth in claim 1 which includes a first resistor and a second resistor in said box and wherein said switch means is movable to a third position which connects said vibrator to said source through both said first and second resistors in series to produce vibration of a still lower amplitude and to deliver heat in a greater amount to said plate.

3. A combined body heating, massaging and spot heating device comprising a cushion containing a vibrator, a switchbox separate from said cushion and containing two resistors, a source of electrical energy, first switching means for electrically connecting said vibrator through said box with said source, said means having four positions one of which connects said source directly with said vibrator, a second of which connects said source in series with one of said resistors and said vibrators, a third of which connects said source in series with both of said resistors and said vibrator and a fourth which provides an open circuit between said source and said vibrator, and a second switching means having four positions one of which connects said source to energize said heating pad at high heat, a second of which connects said source to energize said pad at medium heat, a third of which connects said source to energize said pad at low heat and a fourth of which provides an open circuit between said source and said heating pad, said first and second switching means having only four wires leading to or from said switchbox.

* * * * *